(12) United States Patent
Ross et al.

(10) Patent No.: US 6,606,155 B1
(45) Date of Patent: Aug. 12, 2003

(54) METHOD ANALYSIS FOR THE PRESENCE OF WOOD TREATMENT SUBSTANCES ON WOOD

(75) Inventors: Alan S. Ross, Pittsburgh, PA (US); Hans A. Ward, Wexford, PA (US)

(73) Assignee: Kopcoat, Inc., Pittsburgh, PA (US)

( * ) Notice: Subject to any disclaimer, the term of this patent is extended or adjusted under 35 U.S.C. 154(b) by 0 days.

(21) Appl. No.: 09/628,884

(22) Filed: Jul. 31, 2000

(51) Int. Cl.[7] .............................................. G01N 21/64
(52) U.S. Cl. ...................................... 356/317; 356/417
(58) Field of Search ................................ 356/317, 318, 356/417; 250/458.1, 459.1, 461.1, 461.2

(56) References Cited

U.S. PATENT DOCUMENTS 4,824,483 A * 4/1989 Bumpus ................... 106/18.12
5,023,019 A * 6/1991 Bumpus ..................... 252/607
5,900,944 A   5/1999 Mawby
5,980,593 A * 11/1999 Friswell et al. ............... 44/349

* cited by examiner

*Primary Examiner*—Richard A. Rosenberger
(74) *Attorney, Agent, or Firm*—Debra Z. Anderson; Eckert Seamans Cherin & Mellott, LLC

(57) ABSTRACT

A method of determining the presence and quantity of wood treatment substance (pesticides, water repellants, dimension stabilizers and the like) on wood is provided. The wood treatment substance is combined with a fluorescent material and applied to wood. A light beam is impinged on the wood, and reflected light measured by a spectral device. Color saturation level of the reflected light is determined with a microprocessor. From this measurement a quantity of wood treatment substance on the wood can then be determined.

7 Claims, 3 Drawing Sheets

METHOD ANALYSIS FOR THE PRESENCE OF WOOD TREATMENT SUBSTANCES ON WOOD

BACKGROUND OF THE INVENTION

1. Field of the Invention

This invention relates to a method of analysis for the presence and amount of wood treatment substances, such as pesticides, water repellants or dimensional stabilizers, on or in wood.

2. Description of the Prior Art

U.S. Pat. No. 5,900,944, entitled "Method and Device for the Analysis of Pesticides" discloses and claims a method and device for the quantitative analysis of pesticides on the surface of seeds, and is expressly incorporated herein by a reference.

It has been known for centuries to use wood in building construction, furniture and other products. The aesthetic, functional and economic aspects of wood is products provide many beneficial properties. However, wood is subject to undesirable deterioration due to weather conditions (sun, water, extremes in temperature), pests such as termites, carpenter ants, fungus and others, and additional factors.

It has also long been known to protect wood from such undesirable deterioration. Various substances are available for wood treatment to protect wood from weather conditions, such as water repellants, and from pests. However, there is currently no simple, rapid and cost effective method for determining precisely the presence and quantity of such wood treatment substances on or in wood. To ensure the desired objectives are achieved it is desirable to monitor the presence of these materials on and in wood in effective quantities, depending on the particular substance, type of wood and contemplated end use environment. Methods are needed which are adaptable for in-field analysis, and which are more rapid, cost-effective and simpler to use than currently available methods.

SUMMARY OF THE INVENTION

Accordingly, the present invention provides a method for quantifying the amount of various wood treatment substances present on or in wood. This is accomplished by applying a wood treatment substance in combination with a fluorescent material to the wood A light source impinges a light beam on the wood, light is reflected from the fluorescent material, and the reflected light measured by a spectral device. The color saturation level of the reflected light is determined, and then related to a corresponding amount of wood treatment substance. While not preferred for use in aging studies, the method of the present invention is useful to determine the presence and amount of wood treatment substance on wood while the wood products are on the production line.

It is an object of the invention, therefore, to provide a method of measuring and quantifying an amount of wood treatment substance on the surface of wood.

It is a further object of the invention to provide a method of measuring and quantifying the amount of wood treatment substance present in the interior of a piece of wood.

It is an additional object of the invention to provide such a method in an economical manner that is compatible with existing wood processing techniques.

A further object of the invention is to provide a rapid and accurate analysis method for detecting the presence and amount of wood treatment substances on wood.

An additional object of the invention is to provide such a method taking advantage of modern computer methods and devices.

These and other objects of the invention will become apparent from the following description of the invention, the drawings and the appended claims.

DESCRIPTION OF PREFERRED EMBODIMENTS

As used herein, the term "wood" includes a variety of wood and wood-based materials, including, but not limited to, logs and other types of dried lumber, green lumber, fiberboard, strandboard, laminated veneer lumber, cellulosic composites, plastic wood composites and other types of wood, wood composites and engineered wood formed from wood chips, strands, veneers and adhesives.

As used herein, the term "wood treatment substance" includes, but is not limited to, pesticides (insecticides, fungicides and other pest-reducing agents), water-repellants, dimensional stabilizers, fire retardants and other wood treatment substances used to protect and extend the life of wood products exposed to environmental sources of degradation such as water, sunlight, pests and other agents.

As used herein, the word "thereon" refers to wood treatment substances applied to the surface of the wood or wood treatment substances which have penetrated to the interior of the wood.

As used herein, the term "fluorescent material" includes, but is not limited to, fluorescent colorants, pigments and other materials which are light reflective in the preferred wavelengths of the present invention. The fluorescent material may contain other additives such as surfactants and co-solvents which promote uniform coating, penetration or other desirable properties of the mixture. A preferred fluorescent material is "Invisible Blue," a fluorescent pigment dispersion manufactured by Day-Glo Color Corporation of Cleveland, Ohio, which fluoresces between about 390 nm and 450 nm.

Figure 1:
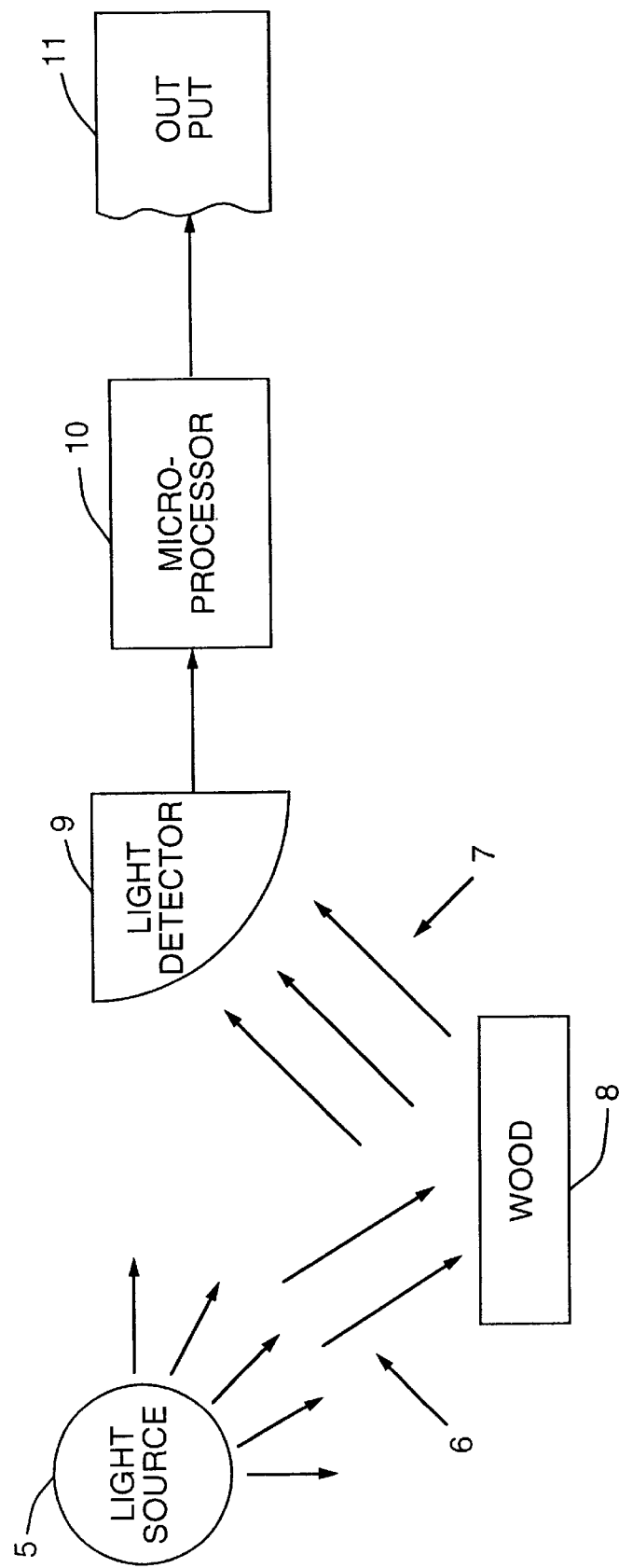
FIG. 1 is a schematic diagram of an embodiment of the method of the present invention.

Referring now to FIG. 1 in greater detail, the present invention provides a method for detecting the quantity or presence of wood treatment substances on or in wood. A preferred embodiment of the method includes impinging a light beam 6 on wood 8 containing a wood treatment substance and a fluorescent material thereon; detecting light 7 reflected from the fluorescent material 9; converting detected light to a corresponding electrical signal in a microprocessor 10, from which an amount of wood treatment substance can be determined. Numerical data or other types of output are then generated 11.

Figure 2:
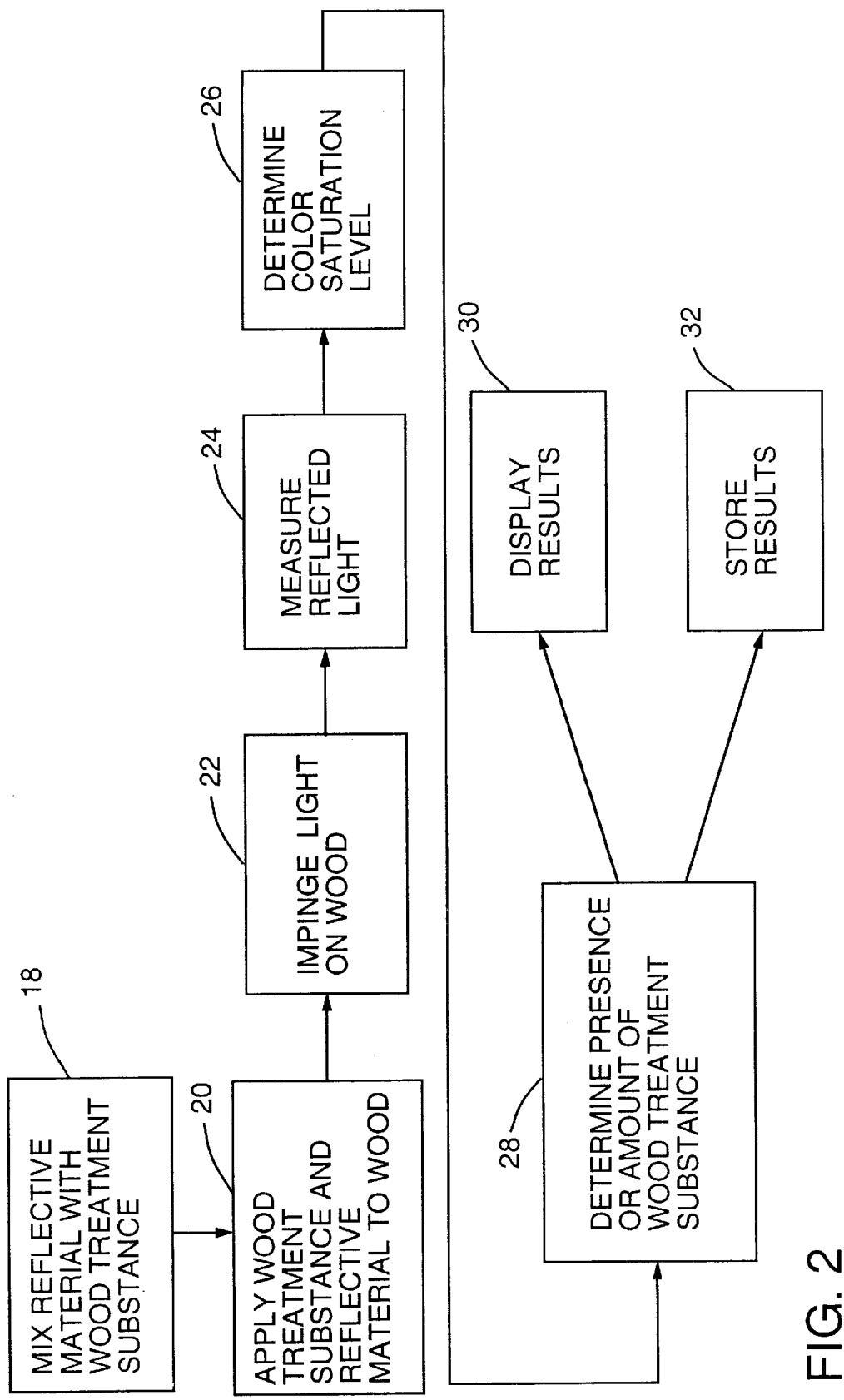
FIG. 2 is a flow diagram of the logical method of an embodiment of present invention.

In FIG. 2 the logical method of an embodiment of the present invention is provided. A fluorescent material is mixed with the wood treatment substance 18. The wood treatment substance and fluorescent material mixture is applied to wood 20. A light beam is impinged on the wood 22. The light reflected from the fluorescent material is measured 24, and a color saturation level determined 26. This is used in turn to determine the amount or presence of wood treatment substance on the wood 28. The output is then displayed 30 or stored 32 for later access.

To arrive at the method of the present invention, a known quantity of a wood treatment substance is mixed with a known quantity of the fluorescent material to form a wood treatment substance and fluorescent material mixture. The wood treatment substance may contain one or more additives which promote uniform coating. The mixture can be sprayed onto the surface of the wood, applied by vacuum or pressure treatment, or the wood can be dipped in the mixture. If the wood is an engineered wood or composite, the chips or strands are treated first, before formation of the composite.

The wood is illuminated and then reflected light is measured by a spectral device. A computer program analyzes the spectral data to determine the presence or amount of the wood treatment substance. Output can be in the form of hard copy (paper) display of numerical data; display via computer monitor of numerical data; or other types of output such as alarm or other audible signal indicating the presence or absence of the wood treatment substance.

Analysis of the treating solution containing the wood treatment substance and ARTS the fluorescent material may also be done prior to its application on the wood, to determine the concentration of the substances in the mixture.

Any source of white light can be used in the present invention to illuminate the wood. A spectral device such as a spectrophotometer, fluorimeter or luminescence scanner is used to measure the light reflected from the reflective coating. Some of the devices (such as the luminescence scanner made by Sick Optic-Electronic, Inc.) both emit and measure reflected light. Any suitable device for measuring light in the wavelengths of interest may be used, and devices which measure light with a wavelength of between about 200–1000 nm are acceptable. The resulting spectral data is analyzed to determine the color saturation level of the reflected light. The color saturation level is then related to a quantity of wood treatment substance on or in the wood.

Where use is intended on composite or engineered wood, the wood treatment substance and fluorescent material combination is mixed with or applied to the wood-based material during processing of the wood chips, strands or veneer prior to formation of the final product. This results in penetration of the wood treatment substance throughout the engineered wood. It is therefore desirable to incorporate a method of testing wherein the wood composite is cut open and the quantity of wood treatment substance on a cross-section of the composite is determined. Such cross sectional testing allows determination of the amount of wood treatment substance which has survived the engineering process, in which materials are often subjected to high heat or pressure treatment.

Figure 3:
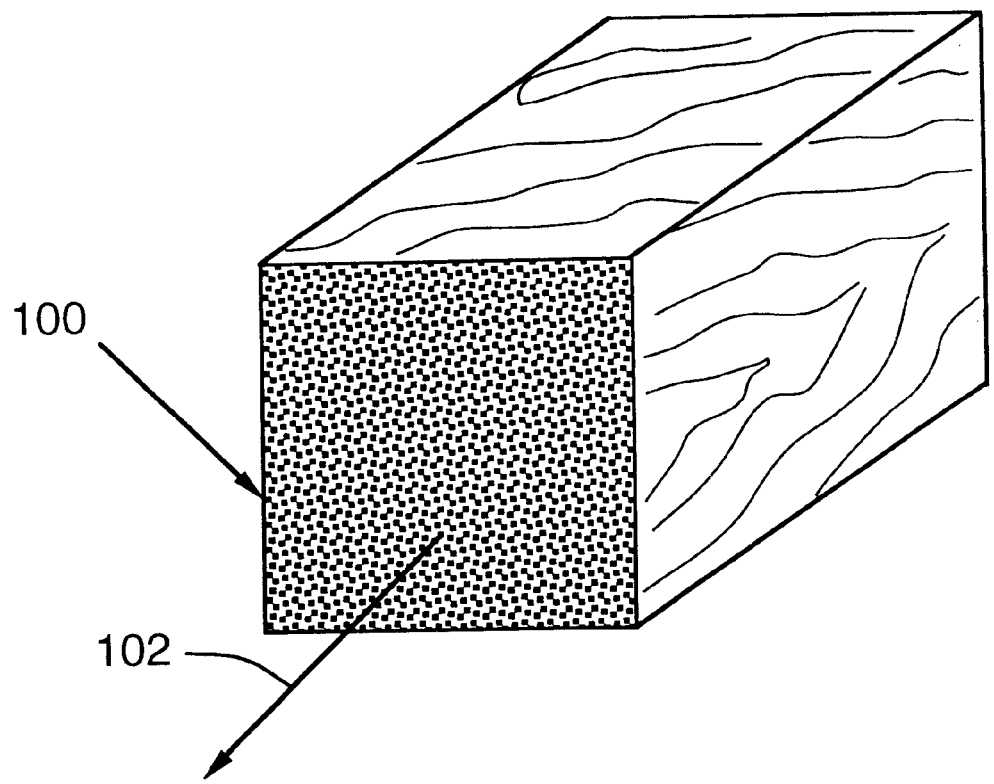
FIG. 3 is an illustration of an additional embodiment of the present invention.

FIG. 3 illustrates this concept. Light is directed to the cut open cross-sectional portion of the wood 100 and reflected light is measured 102 by a spectral device.

The present invention therefore also provides a method for detecting the quantity of wood treatment substances on engineered wood comprising the additional step of severing a portion of the engineered wood and impinging a light beam on a cross-sectional portion of the wood.

EXAMPLE 1

Analysis of Sapstain Control Treatment

In this example, the treatment solution was NP-1® Sapstain Control Chemical (an aqueous mixture of didecyl dimethyl ammonium chloride and 3-iodo-2-propynyl butly carbamate), the substrate was ponderosa pine, the reflective material was Day-Glo® SPL-594N Invisible Blue Fluorescent Pigment Dispersion, and the detection device was a Fluorosense FM-120 fluorimeter equipped with a 360–450 nm detector.

A series of NP-1 in water dilutions was prepared ranging from 50:1 to 300:1 volume: volume. The solutions were analyzed by neutron activation analysis to confirm the specific concentration of IPBC in each. The fluorescent dispersion was added to each solution at one-half the active ingredient level of IPBC. Wafers of ponderosa pine (1 in. by 1 in. by ¼ in.) were dipped for 30 seconds in each solution. The wafers were allowed to air dry overnight. The FM-120 instrument was calibrated with wood wafers treated at the low and high fluorescent pigment levels. Each treated wood wafer was then analyzed using the FM-120 instrument, and the reading in millivolts was recorded. The fluorescence output of each wafer corresponds in a linear fashion to the concentration of the active ingredient and can be displayed graphically. A wafer treated with an unknown amount of NP-1 can be analyzed using the graphical relationship to determine the retention of active ingredient on the surface.

EXAMPLE 2

Analysis of Millwork Preservative Treatment

In this example, the treatment solution was an aqueous dilution of Waterborne Milltreat™ Millwork Preservative (IPBC, active ingredient), the substrate was oriented strandboard, and the reflective material and detection device were as in Example 1. A series of aqueous dilutions of Waterborne Milltreat was prepared ranging in concentration from 0.0% to 0.61% active IPBC. These concentrations were independently confirmed by neutron activation analysis. The reflective material was added to each solution at one-half the concentration of IPBC. Wafers of oriented strandboard (1 in. by 1 in. by ¼ in.) were dipped in each solution and allowed to air dry overnight. The FM-120 instrument was calibrated as in Example 1. Readings were then taken on each treated wafer. Again, the fluorescence output of each treated wafer corresponds in a linear fashion to the concentration of active ingredient on the surface, which can be displayed graphically. A wafer treated with an unknown amount of Waterborne Milltreat can be analyzed using the graphical relationship to determine the retention of active ingredient on the surface.

EXAMPLE 3

Analysis of Wood Composite Treatment

In this example, the substrate was a composite board prepared from aspen flakes, phenol-formaldehyde (PF) resin, and slack wax. The treatment was a liquid dispersion of an insecticide (deltamethrin). The reflective material and detection device were as in Example 1. A series of dilutions of deltamethrin were prepared so as to yield a total board treatment ranging from 10 ppm to 100 ppm by weight. The flakes were blended with the PF resin (5% by weight), slack wax (2% by weight), insecticide (10 to 100 ppm by weight) and the reflective material (0.02%, 0.05%, or 0.10% by weight). Boards were prepared by pre-forming and pressing the pre-form for 15 minutes at 450° at a pressure of 375–400 psi in an electrically heated platen. Board dimensions were 12 in. by 12 in. by ⅜ in.

Wafers of 1 in. by 1 in. by ⅜ in. were cut from the parent boards. The FM-120 instrument was calibrated as in Example 1. Readings were then taken for each fluorescent pigment level in the treated boards. There is a linear relationship between fluorescent pigment concentration in the treated OSB and the readout on the FM-120 fluorimeter.

Whereas particular embodiments of this invention have been described above for purposes of illustration, it will be evident to those skilled in the art that numerous variations of the details of the present invention may be made without departing from the invention as defined in the appended claims.

What is claimed is:

1. A method for detecting the quantity of wood treatment substance on wood comprising the steps of:

impinging a light beam on wood having a wood treatment substance and fluorescent material thereon;

detecting light reflected from said fluorescent material;

converting detected light to a corresponding electrical signal;

employing said electrical signal to determine the color saturation level of the light reflected from said fluorescent material; and determining a quantity of said wood treatment substance from said color saturation level.

2. The method of claim 1, wherein the step of impinging a light beam on the wood comprises illuminating the wood product with electromagnetic radiation having a frequency within the range of 200–1000 nm.

3. The method of claim 1, further comprising severing a portion of said wood and removing a cross-section for testing, prior to impinging the light beam thereon.

4. The method of claim 1, wherein a microprocessor is used to relate the color saturation level of the reflected light to a quantity of wood treatment substance.

5. The method of claim 1, wherein the wood is green lumber.

6. The method of claim 1, wherein the wood is oriented strandboard.

7. The method of claim 1, wherein the fluorescent material is Invisible Blue.

* * * * *

UNITED STATES PATENT AND TRADEMARK OFFICE
CERTIFICATE OF CORRECTION

PATENT NO. : 6,606,155 B1  Page 1 of 1
DATED : August 12, 2003
INVENTOR(S) : Alan S. Ross et al.

It is certified that error appears in the above-identified patent and that said Letters Patent is hereby corrected as shown below:

<u>Column 1,</u>
Line 16, delete "a" prior to "reference".
Line 20, delete "is" prior to "products".
Line 45, insert a -- . -- after "wood".

<u>Column 3,</u>
Line 23, delete the word "ARTS".

Signed and Sealed this

Tenth Day of February, 2004

JON W. DUDAS
*Acting Director of the United States Patent and Trademark Office*